(12) United States Patent
Otero Casal et al.

(10) Patent No.: US 8,586,343 B2
(45) Date of Patent: Nov. 19, 2013

(54) **USE OF BACTERIA OF THE GENUS *TENACIBACULUM* FOR QUORUM QUENCHING**

(75) Inventors: Ana Maria Otero Casal, Santiago de Compostela (ES); Manuel Romero Bernárdez, Santiago de Compostela (ES); Arturo Roca Rivada, Santiago de Compostela (ES)

(73) Assignee: Universidade de Santiago de Compostela, Santiago de Compostela (ES)

( * ) Notice: Subject to any disclaimer, the term of this patent is extended or adjusted under 35 U.S.C. 154(b) by 31 days.

(21) Appl. No.: 13/056,847

(22) PCT Filed: Jul. 23, 2009

(86) PCT No.: PCT/ES2009/070306
§ 371 (c)(1),
(2), (4) Date: Apr. 25, 2011

(87) PCT Pub. No.: WO2010/012852
PCT Pub. Date: Feb. 4, 2010

(65) Prior Publication Data
US 2011/0195051 A1 Aug. 11, 2011

(30) Foreign Application Priority Data
Aug. 1, 2008 (ES) .................................. 200802309

(51) Int. Cl.
*C12N 1/20* (2006.01)
(52) U.S. Cl.
USPC ...................................... 435/252.1; 424/93.4
(58) Field of Classification Search
None
See application file for complete search history.

(56) References Cited

FOREIGN PATENT DOCUMENTS

| WO | 03075654 | 9/2003 |
|---|---|---|
| WO | 2008069374 | 6/2008 |

OTHER PUBLICATIONS

Ahlborn et al., J. Food Prot., vol. 69, No. 4, 2006, pp. 729-738.*
Pineiro-Vidal et al.,(International Journal of Systematic and Evolutionary Microbiology (2008), 58, 881-885.*
Yoon et al., International Journal of Systematic and Evolutionary Microbiology (2005), 55, 793-798.*
Wang et al., International Journal of Systematic and Evolutionary Microbiology (2008), 58, 761-766.*
Sheu et al., International Journal of Systematic and Evolutionary Microbiology (2007), 57, 1148-1153.*
Jung et al., International Journal of Systematic and Evolutionary Microbiology (2006), 56, 1577-1581.*
Altschul et al. "Basic Local Alignment Search Tool", J. Mol. Biol., 1990, vol. 215, pp. 403-410, Academic Press Limited, USA.
Bruhn et al. "Quorum sensing signal molecules (acylated homoserine lactones) in Gram-negative fish pathogenic bacteria*", Diseases of Aquatic Organisms, 2005, vol. 65, pp. 43-52, Inter-Research.
Bruns et al., "Cyclic AMP and Homoserine Lactones Increase the Cultivation Efficiency of Heterotrophic Bacteria from the Central Baltic Sea", Applied and Environmental Microbiology, 2002, pp. 3978-3987, American Society for Microbiology, USA.
Carpentier et al., "Biofilms and their consequences, with particular reference to hygiene in the food industry", journal of Applied Bateriology, 1993, vol. 75, pp. 499-511, France.
Chio et al. "*Tenacibaculum litoreum* sp. nov., isolated from tidal flat sediment", Intl Journal of Systematic and Evolutionary Microbiology, 2006, vol. 56, pp. 635-640, IUMS, Great Britain.
Costerton et al. "Baterial Biofilms: A Common Cause of Persistent Infections", Science, 1991, vol. 284, pp. 1318-1322, American Association for the Advancement of Science, USA.
Dong et al. "Quorum-quenching microbial infections: mechanisms and implications", Phil Trans. R. Soc. B, 2007, vol. 362, pp. 1201-1211, The Royal Society.
Dong et al., "Quorum Sensing and Quorum-Quenching Enzymes", The Journal of Microbiology, 2005, vol. 43, pp. 101-109, The Microbiological Society of Korea.
Frette et al., "*Tenacibaculum skagerrakense* sp. nov., a marine bacterium isolated from the pelagic zone in Skagerrak, Denmark", Intl Journal of Systematic and Evolutionary Microbiology, 2004, vol. 54, pp. 519-524, IUMS, Great Britain.
Fuqua et al., "Quorum Sensing in Bacteria: the LuxR-LuxI Family of Cell Density-Responsive Transcriptional Regulators", Journal of Bacteriology, 1994, vol. 176, No. 2, pp. 269-275, American Society for Microbiology.
Givskov et al., "Eukaryotic Interference with Homoserine Lactone-Meditated Prokaryotic Signalling", Journal of Bacteriology, 1996, vol. 178, No. 22, pp. 6618-6622, American Society for Microbiology.
Hansen et al., "*Flexibacter ovolyticus* sp. nov., a Pathogen of Eggs and Larvae of Atlantic Halibut, *Hippoglossus hippoglossus* L.", Intl Journal of Systematic Bacteriology, 1992, vol. 42, No. 3, pp. 451-458, Intl union of Microbiological Societies, Norway.
Heindl et al., "*Tenacibaculum adriaticum* sp. nov., from a bryozoan in the Adriatic Sea", Intl Journal of Systematic and Evolutionary Microbiology, 2008, vol. 58, pp. 542-547, IUMS, Great Britain.
Jung et al., "*Tenacibaculum aestuarii* sp. nov., isolated from a tidal flat sediment in Korea", Intl Journal of Systematic and Evolutionary Microbiology, 2006, vol. 56, pp. 1577-1581, IUMS, Great Britain.
McClean et al., "Quorum sensing and *Chromobacteriurm violaceum*: exploitation of violacein production and inhibition for the detection of N-acyl homoserine lactones", Microbiology, 1997, vol. 143, pp. 3703-3711, SGM, Great Britain.
Milton et al., "The LuxM Homologue VanM from *Vibrio anguillarum* Directs the Synthesis of N-(3-Hydroxyhexanoyl) homoserine Lactone and N-Hexanoylhomoserine Lactone", Journal of Bacteriology, 2001, vol. 183, No. 12, pp. 3537-3547, American Society for Microbiology, UK.

(Continued)

*Primary Examiner* — Irene Marx
(74) *Attorney, Agent, or Firm* — Gardner, Groff, Greenwald & Villanueva, P.C.

(57) ABSTRACT

Use of bacterial cells of the genus *Tenacibaculum*, from the crude cellular extract or from its cultivation supernatants, capable of degrading N-acyl homoserine lactones, for quorum quenching, for treatment of infectious bacterial illnesses or to inhibit formation of biofilms.

3 Claims, 4 Drawing Sheets

(56) References Cited

OTHER PUBLICATIONS

Morin et al. "O n-line high-performance liquid chromatography—mass spectrometric detection and quantification of N-acylhomoserine lactones, quorum sensing signal molecules, in the presence of biological matrices", Elsevier, 2003, vol. 1002, pp. 79-92, Elsevier Science B.V.

Morohoshi et al., "N-Acylhomoserine lactone regulatesviolacein production in *Chromobacterium violaceum* type strain ATCC 12472", FEMS Microbiol Lett, 2008, vol. 279, pp. 124-130, Blackwell Publishing Ltd.

Pinerio-Vidal et al., "*Tenacibaculum discolor* sp. nov. and *Tenacibaculum gallaicum* sp. nov., isolated from sole (*Solea senegalensis*) and turbot (*Psetta maxima*) culture systems", Intl Journal of Systematic and Evolutionary Microbiology, 2008, vol. 58, pp. 21-25, IUMS, Great Britain.

Pinerio-Vidal et al., "*Tenacibaculum soleae* sp. nov., isolated from diseased sole (*Solea senegalensis* Kaup)", Intl Journal of Systematic and Evolutionary Microbiology, 2008, vol. 58, pp. 881-885, IUMS, Great Britain.

Schut et al., "Isolation of Typical Marine Bacteria by Dilution Culture: Growth, Maintenance, and Characteristics of Isolates under Laboratory Conditions", Applied and Environmental Microbiology, 1993, vol. 59, No. 7, pp. 2150-2160, American Society for Microbiology.

Sheu et al., "*Tenacibaculum liitopenaei* sp. nov. isolated from a shrimp mariculture pond", Intl Journal of Systematic and Evolutionary Microbiology, 2007, vol. 57, pp. 1148-1153, IUMS, Great Britain.

Suzuki et al., "Phylogenetic analysis and taxonomic study of marine Cytophaga-like bacteria: proposal for *Tenacibaculum* gen. nov. with *Tenacibaculum maritimum* comb. nov. and *Tenacibaculum ovolyticum* comb. nov., and description of *Tenacibaculum mesophilum* sp. nov. and *Tenacibaculum amylolyticum* sp. nov.", Intl Journal of Systematic and Evolutionary Microbiology, 2001, vol. 51, pp. 1639-1652, IUMS, Great Britain.

Uroz et al., "N-Acylhomoserine lactone quorum-sensing molecules are modified and degraded by *Rhodococcus erythropolis* W2 by both amidolytic and novel oxidoreductase activities", Microbiology, 2005, vol. 151, pp. 3313-3322, SGM, Great Britain.

Venturi, "Regulation fo quorum sensing in *Pseudomonas*", FEMS Microbiol Rev, 2006, vol. 30, pp. 274-391, Blackwell Publishing Ltd.

Wakabayashi et al., "*Flexibacter maritimus* sp. nov., a Pathogen of Marine Fishes", Intl Journal of Systematic Bacteriology, 1986, vol. 36, No. 3, pp. 396-398, Intl Union of Microbilogical Societies.

Wang et al., "*Tenacibaculum aiptasiae* sp. nov., isolated from a sea anemone *Aiptasia pulchella*", Intl Journal of Systematic and Evolutionary Microbiology, 2008, vol. 58, pp. 716-766, IUMS, Great Britain.

Whitehead et al., "Quorum-sensing in Gram-negative bacteria", FEMS Microbiology Reviews, 2001, vol. 25, pp. 365-404, Elsevier Science B.V.

Williams et al., "Look who's talking: communication and quorum sensing in the bacterial world", The Royal Society, 2007, vol. 362, pp. 1119-1134, Phil. Trans. R. Soc. B.

Winson et al. "Construction and analysis of luxCDABE-based plasmid sensors for investigating N-acyl homoserine lactone-mediated quorum sensing", FEMS Microbiology Letters, 1998, vol. 163, pp. 185-192, Elsevier Science B.V.

Yates et al. "N-Acylhomoserine Lactones Undergo Lactonolysis in a pH-, Temperature-, and Acyl Chain Length-Dependent Manner during Growth of *Yersinia pseudotuberculosis* and *Pseudomonas aeruginosa*", Infection and Immunity, 2002, vol. 70, No. 10, pp. 5635-5646, American Society for Microbiology.

Yoon et al. "*Tenacibaculum lutimaris* sp. nov., isolated from a tidal flat in the Yellow Sea, Korea", Intl Journal of Systematic and Evolutionary Microbiology, 2005, vol. 5, pp. 793-798, IUMS, Great Britain.

International Search Report dated Oct. 22, 2009 for international application No. PCT/ES2009/070306.

Lin Y. et al., "Acyl-homoserine lactone acylase from *Ralstonia* strain XJ12B represents a novthe and potent class of quorum-quenching enzymes." Molecular Microbiology. 2003, vol. 47, pp. 849-860.

Hentzer M et al. Pharmacological inhibition of qourum sensing for the treatment of chronic bacterial infections. The Journal of Clinical Investigation. Nov. 2003, vol. 112, pp. 1300-1307. DOI: 10.1172/JCI200320074.

\* cited by examiner

SEQUENCE LISTING

<160> NUMBER OF SEQ ID NOS: 1

<210> SEQ ID NO 1
<211> LENGTH: 1019
<212> TYPE: DNA
<213> ORGANISM: Tenacibaculum discolor

<400> SEQUENCE: 1

```
catgcaagtc gagggtaac agggaaaagc ttgcttttt gctgacgacc ggcgaacggg      60
tgcgtaacgc gtatagaatc tgccttgtac aggaggatag cctttagaaa tgaagattaa    120
tactccataa tgttgagaga tggcatcatc ttttaattaa agatttatcg gtacaagatg    180
actatgcgtc ctattagcta gatggtaagg taacggctta ccatggcaac gataggtagg    240
gggtctgaga ggattatccc ccacactggt actgagacac ggaccagact cctacgggag    300
gcagcagtga ggaatattgg tcaatggagg caactctgaa ccagccatgc cgcgtgcagg    360
aagactgccc tatggttgt aaactgcttt tatacaggaa gaaacttagt tacgtgtaac    420
taactgacgg tactgtaaga ataagcaccg gctaactccg tgccagcagc cgcggtaata    480
cggagggtgc aagcgttatc cggaatcatt gggtttaaag ggtccgcagg cggtcaatta    540
agtcagaggt gaaatcccat agcttaacta tggaactgcc tttgatactg gttgacttga    600
gttatacgga agtagataga ataagtagtg tagcggtgaa atgcatagat attacttaga    660
ataccgattg cgaaggcagt ctactacgta tatactgacg ctcatggacg aaagcgtggg    720
gagcgaacag gattagatac cctggtagtc cacgccgtaa acgatggaca ctagttgttg    780
ggattattct cagtgactaa gcgaaagtga taagtgtccc acctggggag tacgatcgca    840
agattgaaac tcaaaggaat tgacggggc ccgcacaagc ggtggagcat gtggtttaat    900
tcgatgatac gcgaggaacc ttaccagggc ttaaatgtag agtgacagac tgagagatcg    960
gttttcttc ggacacttta caaggtgctg catggttgtc gtcagctcgt gccgtgagg   1019
```

USE OF BACTERIA OF THE GENUS *TENACIBACULUM* FOR QUORUM QUENCHING

IN THE CROSS-REFERENCE TO RELATED APPLICATIONS

This application claims priority to Spanish Application No. P200802309, filed Aug. 1, 2008, which is hereby incorporated by reference in its entirety for all purposes.

REFERENCE TO SEQUENCE LISTING

The present application is being filed along with a Sequence Listing. A polypeptide sequence is described herein and is referred to by a sequence identifier number (SEQ ID NO). The SEQ ID NO corresponds numerically to the sequence identifier <400>1. The copy of the Sequence Listing, being submitted electronically with this patent application, provided under 37 CFR §1.821-1.825, is a read-only memory computer-readable file in ASCII text format. The Sequence Listing is named "08_Sequence_listing.txt", the electronic file of the Sequence Listing was created on Feb. 9, 2011, and is 2 kilobytes in size as measured in MS-WINDOWS. The Sequence Listing is hereby incorporated by reference in its entirety.

The present invention is included in the field of biology and molecular biology, and relates to species of the genus *Tenacibaculum* capable of degrading N-acyl-homoserine lactones (AHLs) for the control of infectious bacterial diseases, and for avoiding the formation of biofilms.

STATE OF PRIOR ART

Numerous bacterial species use a coordinated genetic regulation mechanism to respond to changes in the environment. This mechanism, known as quorum sensing (OS), consists in the production and release of signal molecules to the medium where they accumulate controlling the expression of multiple genes (Fuqua et al., 1994. *J Bacteriol* 176: 269-275). By means of communication by OS, the bacterial populations can be coordinated in order to execute important biological functions, many of them involved in the virulence of important pathogens, such as: mobility, swarming, aggregation, luminescence, biosynthesis of antibiotics, virulence factors, symbiosis, formation and differentiation of biofilms, transfer of plasmids by conjugation, etc. (Williams et al., 2007. *Phil Trans R Soc* B 362: 1119-1134).

The OS signals most widely studied and known are N-acyl-homoserine lactones (AHLs) used by numerous Gram-negative bacteria (Williams et al., 2007. *Phil Trans R Soc* B 362: 1119-1134). AHLs, also known as autoinducers (AIs), are a family of signal molecules used in the OS system of many bacteria, mainly Gram negative, which are based on a lactone ring with a side acyl chain of variable size between 4 and 14 carbons, with or without saturation and with or without Oxo- or Hydroxy-substitutions in the third carbon (Whitehead et al., 2001. *FEMS Microbiol Rev* 25: 365-404). As the populations of bacterial species coordinated by OS obtain important competitive advantages in their multiple interactions with other prokaryotes and eukaryotes, their competitors have developed mechanisms to interfere with their communication by OS systems; these mechanisms are known as quorum quenching (QQ). They are based on the production of inhibitors that mimic AHLs blocking the receptor, such as the furanones produced by the marine algae *Delisea pulchra* (Givskov et al., 1996. *J Bacteriol* 178: 6618-6622). Another strategy to block the QS systems mediated by AHLs is the enzymatic degradation of the signal molecules. To date, two main types of enzymes have been described that carry out this degradation: lactonases that hydrolyze the lactone ring and acylases that break the bond between the lactone ring and the side chain (Dong et al., 2007. *Phil Trans R Soc* B 362: 1201-1211).

Although the synthesis of artificial chemotherapies and the discovery and improvement of antibiotics has meant, in the last century, a genuine medical revolution in the treatment of infectious diseases, the development of antibiotic resistance by some pathogenic bacteria is a serious global problem, which forces the pharmaceutical industry to develop new generations of more potent antibiotics, and which may give rise to multi-resistance strains wherein treatment is longer and frequently ineffective, even leading to the death of the patient. The selective pressure exercised in the microbial environment, the immune condition of the host, the bacterial micro-environments and typical factors of the bacteria involved play an important role in the development of resistance.

Since the great quantity of human pathogens (e.g.: *Pseudomonas putida*, *Serratia* spp, . . . ), plant pathogens (e.g.: *Agrobacterium* spp., *Erwinia carotovora*, . . . ) and marine pathogens (e.g.: *Aeromonas salmonicida*, *Vibrio anguillarum*, . . . ) (Williams et al., 2007. *Phil Trans R Soc* B 362: 1119-1134; Bruhn et al., 2005. *Dis Aquat Org* 65: 43-52.) use AHLs for the production control of virulence factors, interference with these communication systems constitutes an interesting and promising channel for the control of infectious bacterial diseases (Dong & Zhang. 2005. *J Microbiol* 43: 101-109; Dong et al., 2007. *Phil Trans R Soc* B 362: 1201-1211). Furthermore, this type of mechanism in combination with antibiotics may be an interesting strategy in the treatment of infectious diseases by multiresistant pathogens such as *Pseudomonas aeruginosa*, in which QS control on virulence mechanisms has been described (Venturi, 2006. *FEMS Microbiol Rev* 30: 274-291), and other human, animal and plant pathogens. The interest of the QQ strategies for the treatment of infectious diseases is that, since they do not directly affect survival of the pathogen but the expression of the virulence factors, they do not exert selective pressure, avoiding the appearance of resistances.

DESCRIPTION OF THE INVENTION

The selective pressure represented by the large scale application of chemotherapies has enabled the dissemination of microbial strains with mechanisms of resistance that, on many occasions, hinder the suitable clinical treatment, even leading to the death of the patient. Since many bacteria use the QS signal system to synchronize the genetic expression and coordinate the biological activity within a population, controlling the virulence and formation of biofilms among other biological functions, a channel to avoid the increase of mechanisms of resistance of the pathogenic bacteria would be to control these QS signal systems. The inhibition of this signal system is what has been called Quorum Quenching (QQ). The present invention provides the means to control bacterial infections, without exerting selective pressure on the populations of these bacteria and thus avoiding the appearance of resistances as well as for the inhibition of other bacterial colonization processes wherein QS signals, AHL type, are involved, such as the formation of biofilms. The present invention discloses for the first time the use of bacterial cells of the genus *Tenacibaculum* capable of degrading N-Acyl-homoserine lactones (AHLs), to control infectious bacterial diseases and to inhibit the formation of biofilms.

Thus, a first aspect of the invention relates to the use of the bacterial cells of the genus *Tenacibaculum*, of the crude cellular extract or of its cultivation supernatants, or any of their combinations, for quorum quenching.

In a preferred embodiment of this aspect of the invention, the bacterial cells of the genus *Tenacibaculum*, the crude cellular extract or its cultivation supernatants, or any of their combinations, are used to degrade N-Acyl-homoserine lactones (AHLs).

Any bacterium regulates its gene expression in response to different environmental signals, which is an essential property to compete with other organisms. In the particular case of pathogenic bacteria, gene regulation is vital in allowing the bacteria to survive in the particular environment which is offered by their host. The bacterial virulence genes are subject to complex regulation mechanisms to ensure expression of the appropriate gene at the appropriate time. AHLs are the QS signals most widely studied and known, and are used by multitude human, plant and marine pathogenic bacteria in order to control the production of virulence factors.

Therefore, a preferred embodiment of this aspect of the invention is the use of the bacterial cells of the genus *Tenacibaculum*, of the crude cellular extract or of the cultivation supernatant of said bacteria of the genus *Tenacibaculum*, or any of their combinations, which are capable of degrading N-acyl homoserine lactones, and that therefore interfere with the QS signal system of bacteria, for the manufacture of a medicament. In an even more preferred embodiment, the medicament is used for the treatment of infectious bacterial diseases.

"Biofilms", as defined in this specification, are communities of microorganisms that grow embedded in a matrix of exopolysaccharides and adhered to an inert surface or a living tissue. It is a community of bacteria (of a single species or several), that is adhered to a solid surface. Inhibition of AHLs would make it possible to inhibit the formation of biofilms formed by processes controlled by QS.

Biofilms produce a large amount of extracellular polysaccharides, responsible for the viscous appearance, and they are characterized in that they have a great resistance to antibiotic agents. This resistance may be due to the fact that the extracellular matrix wherein the bacteria are embedded provides a barrier to the penetration of biocides. Another possibility is that the majority of the biofilm cells grow very slowly, in a state of food deprivation, which means they are not susceptible to the effect of antimicrobial agents. A third aspect could be that the cells in the biofilm adopt a different phenotype, for example, by the expression of effluent pumps of drugs.

The biological contamination of surfaces is common, and the biofilm can develop on hydrophobic, hydrophilic, biotic or abiotic surfaces, leading to the degradation of the material, contamination products, mechanical blocking and impedance of heat transfer in aquatic processes. Biofilms are also the first cause of biological contamination of drinking water distribution systems, and other pipes, with the control of biofilms in fire prevention systems being especially important. The establishment of bacteria adhered to food or surfaces in contact with food entails serious hygiene problems and even cases of food toxi-infection, as well as numerous financial losses due to the products discarded (Carpentier & Cerf, 1993. *J App Bacter.* 75:499-511).

In fish farming, biofilm formation is particularly relevant in submerged structures such as cages, nets and containers; or equipment such as pipes, pumps, filters and collection tanks and for cultivated species, such as mussels, scallops, oysters, etc. This is known as biofouling and affects all sectors of European fish farming, being a growing problem due to the application of the Biocidal Products Directive EC 98/8/EC, resulting in substantial economic losses. It also has important ecological repercussions as the aquatic organisms incrusted on the hulls of boats as a consequence of biofouling accompany these boats wherever they go. This has meant a global ecological problem, since the boats are transferring invading species towards the lakes, rivers and oceans that are not their original habitat.

Thus, the manufacture of anti-incrustation paint with bacterial cells of the genus *Tenacibaculum*, the crude cellular extract or the cultivation supernatant of said bacteria would reduce biofouling in the hulls painted with it, without having chemical elements that are toxic for marine life.

Therefore, in another preferred embodiment, the bacterial cells of the genus *Tenacibaculum*, the crude cellular extract or the cultivation supernatant of said bacteria of the genus *Tenacibaculum*, are used to inhibit the formation of biofilms.

There is numerous epidemiological evidence that links biofilms to different infectious processes in humans (Table 1) (Wilson, 2001. *Sci Prog* 84: 235-254; Costerton et al., 1999. *Science* 1999; 284: 1318-1322). The mechanisms whereby the biofilm produces the symptoms of the disease are still not completely established, but it has been suggested that the biofilm bacteria may produce endotoxins, that can release groups of bacteria into the bloodstream, become resistant to the phagocytic action of the immune system cells and, on the other hand, constitute a niche for the appearance of bacteria resistant to antibiotic treatment. This last aspect may be especially relevant since the resistant bacteria originated in a biofilm could extend from patient to patient by means of the hands of the healthcare personnel.

Furthermore, this type of mechanism in combination with antibiotics may be an interesting strategy in the treatment of infectious diseases by multiresistant pathogens such as *Pseudomonas aeruginosa*, wherein the control of QS on virulence mechanisms has been described (Venturi, 2006. FEMS Microbiol Rev 30: 274-291), and other pathogens of humans, animals and plants. Therefore, an even more preferred embodiment of this aspect of the invention is the use of the bacterial cells of the genus *Tenacibaculum*, of the crude cellular extract or of the cultivation supernatant of said bacteria of the genus *Tenacibaculum*, which are capable of degrading N-acyl homoserine lactones, in combination with antibiotics, for the treatment of infectious bacterial diseases or for inhibiting the formation of biofilms.

TABLE 1

Human infectious processes wherein biofilm formation intervenes.

| Infection or disease | Bacterial species forming the biofilm |
| --- | --- |
| Dental caries | Acidogenic Gram positive cocci (e.g. *Streptococcus*) |
| Periodontitis | Gram negative oral anaerobic bacteria |
| Otitis media | Non-typable strains of *Haemophilus influenzae* |
| Infections of the musculoskeletal system | Gram positive cocci (e.g. *Staphylococcus*) |
| Necrotizing fasciitis | *Streptococcus* group A |
| Osteomielitis | Several bacterial and fungal species |
| Bacterial prostatitis | *E. coli* and other Gram negative bacteria |
| Native valve endocarditis | *Streptococci* of the viridans group |

TABLE 1-continued

Human infectious processes wherein biofilm formation intervenes.

| | Bacterial species forming the biofilm |
|---|---|
| Pneumonia due to cystic fibrosis | *Pseudomonas aeruginosa* and *Burkholderia cepacia* |
| Meloidosis | *Pseudomonas pseudomallei* |
| Nosocomial diseases | |
| Pneumonia (intensive care) | Gram negative bacilli |
| Sutures | *Staphylococcus epidermidis* and *S. aureus* |
| Exit orifices | *S. epidermidis* and *S. aureus* |
| Arteriovenous channels | *S. epidermidis* and *S. aureus* |
| Scleral buckle | Gram positive cocci |
| Contact lenses | *P. aeruginosa* and other Gram positive cocci |
| Cystitis due to urinary catheters | *E. coli* and other Gram negative bacilli |
| Periodontitis due to peritoneal dialysis | A variety of bacteria and fungi |
| IUD | *Actinomyces israelli* and many others |
| Endotracheal tubes | A variety of bacteria and fungi |
| Hackman catheters | *S. epidermidis* and *Candida albicans* |
| Central venous catheters | *S. epidermidis* and others |
| Mechanical heart valves | *S. epidermidis* and *S. aureus* |
| Vascular grafts | Gram positive cocci |
| Blocking of the bile duct | A variety of enteric bacteria and fungi |
| Orthopaedic devices | *S. epidermidis* and *S. aureus* |
| Penis prosthesis | *S. epidermidis* and *S. aureus* |

Figure 1:
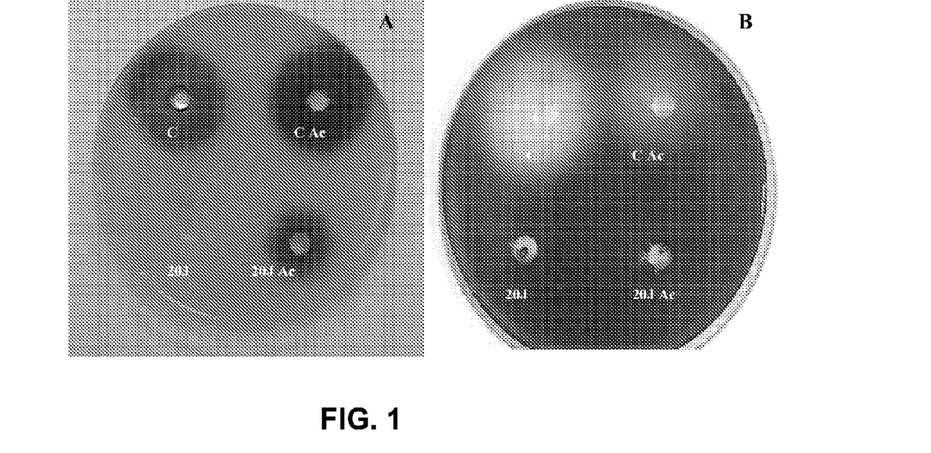
FIG. 1. Assay with *Chromobacterium violaceum* CV026 to detect degradation by *Tenacibaculum discolor* 2OJ of 2 μM C6-HSL (A) and C10-HSL (B) related to controls before (C) and after acidifying to pH 2.0 (C Ac).

The bacteria of the genus *Tenacibaculum* of the invention is characterized in that they are capable of degrading AHLs. In order to carry out the present invention, different strains of different species of the genus *Tenacibaculum* were assayed. Thus, for example, this AHL degrading activity was detected in different assays with biosensors: *Chromobacterium violaceum* CV026 with the AHLs: N-Hexanoyl-L-homoserine lactone (C6-HSL) (FIG. 1A) and C10-HSL (FIG. 1B), *Escherichia coli* JM109 pSB536 or pSB1075 with the AHLs: C4 and C12-HSL, and confirmed by liquid chromatography-mass spectrometry (LC-MS) with the AHLs C4, C6, C8, C10, C12 and C14-HSL (for C4 and C12-HSL, FIG. 2).

The information provided in this specification is sufficient to allow a person skilled in the art to identify other strains and other species within this genus.

The genus *Tenacibaculum* was described by Suzuki et al. in 2001 (Suzuki et al., 2001. *Int J Syst Evol Microbiol*, 51: 1639-1652) based on its phylogenetic, chemotaxonomic and phenetic characteristics, combining two species of the genus *Flexibacter* (*F. maritimus* and *F. ovolyticus*) and describing *Tenacibaculum maritimum* as the type specie, and another two new species for the genus, *Tenacibaculum mesophilum* and *Tenacibaculum amylolyticum*. Subsequently, other species have been added to the genus, so that a total of 14 accepted species exist at the date of drafting this specification:

*Tenacibaculum adriaticum* Heindl et al. 2008.
*Tenacibaculum aestuarii* Jung et al. 2006.
*Tenacibaculum aiptasiae* Wang et al. 2008.
*Tenacibaculum amylolyticum* Suzuki et al. 2001.
*Tenacibaculum discolor* Piñeiro-Vidal et al. 2008.
*Tenacibaculum gallaicum* Piñeiro-Vidal et al. 2008.
*Tenacibaculum litopenaei* Sheu et al. 2007.
*Tenacibaculum litoreum* Choi et al. 2006.
*Tenacibaculum lutimaris* Yoon et al. 2005.
*Tenacibaculum maritimum* (Wakabayashi et al. 1986) Suzuki et al. 2001.
*Tenacibaculum mesophilum* Suzuki et al. 2001.
*Tenacibaculum ovolyticum* (Hansen et al. 1992) Suzuki et al. 2001.
*Tenacibaculum skagerrakense* Frette et al. 2004.
*Tenacibaculum soleae* Piñeiro-Vidal et al. 2008.

Due to the special characteristics of these organisms, which have still not been studied in depth, and due to the difficulties involved in their description, it will be easier and more reliable if their taxonomic delimitation is based on molecular biology methods.

Thus, the following parameters are applicable in the identification of a microorganism as belonging to the genus *Tenacibaculum*, whether in isolation or in combination with the previous ones. Since the strains of *Tenacibaculum* are similar in terms of their evolution, it can be expected that the global homology of the genomes at a nucleotide level, and more specifically at the level of the 16S region of the nuclear ribosomal RNA, and more specifically to the polynucleotide of the 16S region of the nuclear ribosomal RNA included in SEQ ID NO: 1, and which belongs to the microorganism deposited in the Collección Española de Cultivos Tipo (CECT) on 18 Jun. 2008 (accession number 7426) and which in this document is called *T. discolor* 2OJ strain, is 80% or greater, and more preferably is 85%, 90%, 95% or greater. The correspondence between the genome sequence of the putative strain(s) of *Tenacibaculum* and the sequence of another microorganism can be determined by methods known in the state of the art. For example, the former can be determined by the direct comparison of the polynucleotide sequence information from the putative *Tenacibaculum*, and the polynucleotide sequence of SEQ ID NO: 1 of this specification. The sequence comparison methods are known in the state of the art, and include, but are not limited to, the program BLASTP or BLASTN, and FASTA (Altschul et al., 1999. *J Mol Biol* 215: 403-410). For example, also, the former can be determined by hybridation of the polynucleotides in conditions which form stable duplexes between homologous regions, followed by digestion with specific single-stranded nuclease(s), followed by determination of the size of the digested fragments.

The percentage of homology has been determined by measuring the identity between the polynucleotide shown in SEQ ID NO: 1 (belonging to the strain of the genus *Tenacibaculum* deposited in the CECT) and all homologous polynucleotides of the genus *Tenacibaculum* which are found at the time of writing this specification, in the GenBank. After this analysis it could be thought that an organism belonging to the genus *Tenacibaculum* will have a polynucleotide homologous to that of SEQ ID NO: 1, belonging to the 16S region of its nuclear ribosomal RNA, which has, at least, an 80% identity therewith.

Another aspect of the invention relates to a strain of bacterial cells of the genus *Tenacibaculum*, which have been deposited in the Spanish Type Culture Collection (CECT), with number CECT 7426. Said bacterial strain has been identified as belonging to the species *Tenacibaculum discolor*, and the sequence of polynucleotides of the ribosomal region 16S is partially included in SEQ ID NO: 1.

In relation to other strains of bacteria with QQ activity, the strain with deposit number CECT 7426 has a high degrading activity, high non-specificity, is capable of degrading all the AHLs tested with chains of between 4 and 14 carbons in a period of 24 hours according to data obtained by LC-MS quantification, shows good growth, capacity of growth in marine and non-marine media and a constitutive QQ activity arising from the immediate degradation of AHLs (the exposure of bacteria to AHLs is not necessary for it to be activated).

Figure 4A:
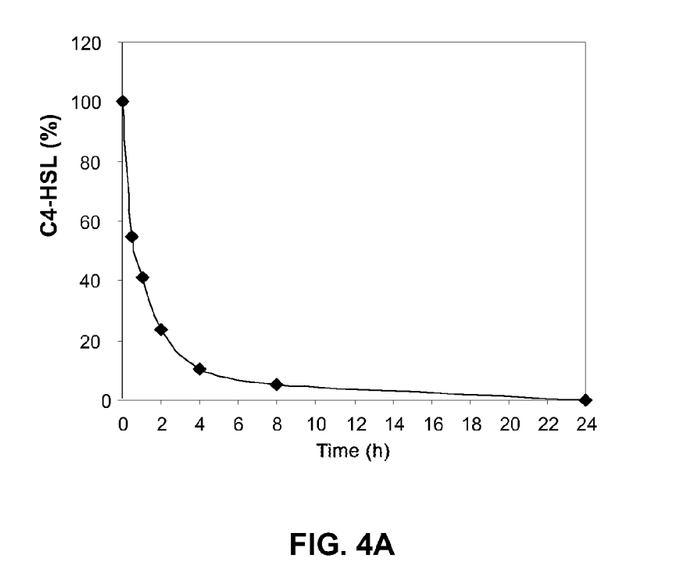
FIG. 4. Degradation kinetics of C4-HSL (4A) and C12-HSL (4B) by living cultures of the strain *T. discolor* 2OJ measured by LC-MS. Initial concentration of the AHLs: 30 μM.
Figure 4B:
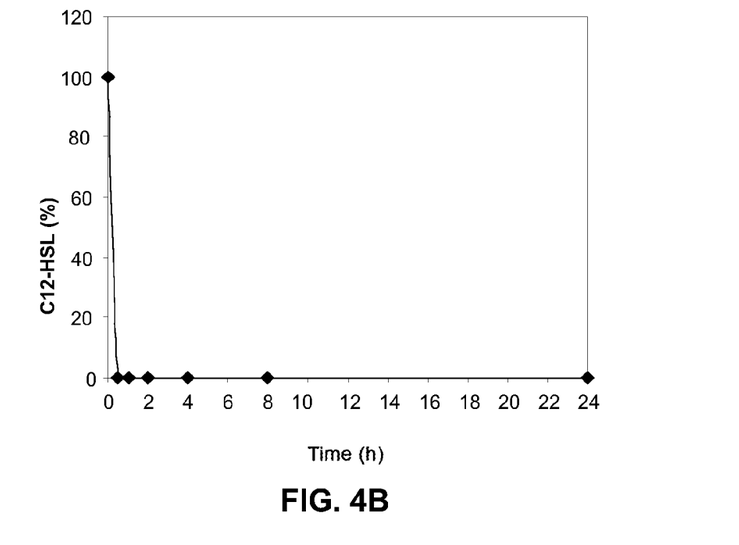
Figure 5A:
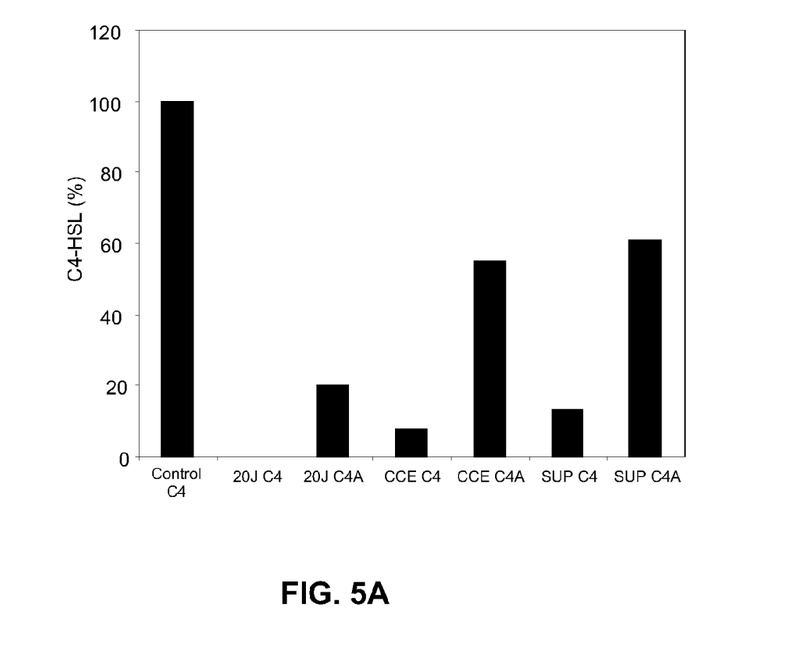
FIG. 5. Degradation activity of C4-HSL (5A) and C12-HSL (5B) in complete cell cultures of the strain *T. discolor* 2OJ, crude cellular extracts (CCE) and supernatant (SUP) after 24 hours. The quantification of the AHLs was carried out by LC-MS. The extracts were measured with and without acidification to estimate the degree of possible lactonase activity that was present. Initial concentration of the AHLs: 50 μM.
Figure 5B:
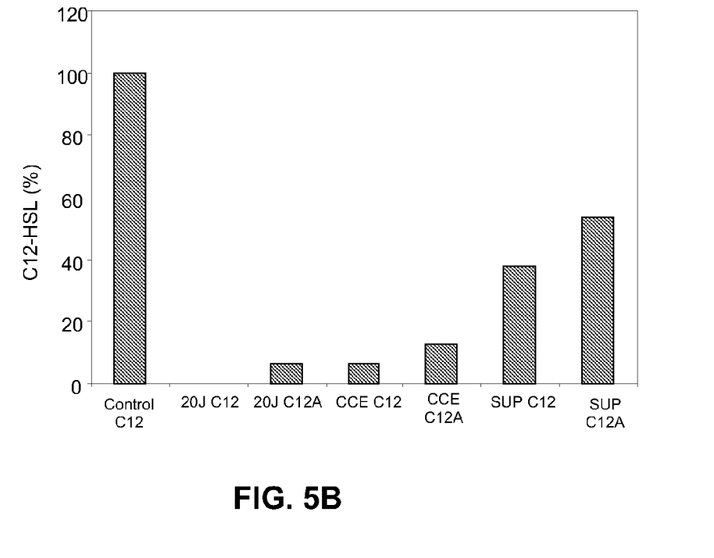

We tried to determine the type of enzymatic activity of *Tenacibaculum discolor* of the strain deposited with access number CECT 7426; in order to do so, the pH was acidified to 2.0 after the degradation. A recovery of C4 (FIG. 2) and C6-HSL (FIG. 1A) was observed after acidification, indicating a lactonase-type activity, because the acidic pH closes the lactone ring. Nevertheless, 010-HSL (FIG. 1B) and C12-HSL (FIG. 2) were not recovered, which indicates the presence of a dual enzymatic activity: lactonase for short side chain AHLs and acylase for long side chain AHLs. This is supported by the different degradation kinetics observed for 30 µM C4-HSL and C12-HSL, which were determined by LC-MS (FIG. 4). The 2OJ strain degrades all the C12 in 30 min and C4 in 8 hours (FIG. 4). The degrading activity is found both in the supernatant and in the crude cellular extract (CCE) of cultures (FIG. 5), which enables the use of the live strain or crude or purified cell extracts for their biotechnological applications.

The high degrading capacity and wide range of specificity shown by the enzymes of the bacteria of the genus *Tenacibaculum*, members of the group Cytophaga-Flexibacter-Bacteroidetes (CFB), against the range of sizes of AHL side chain: C4-C14, makes it a promising candidate for the control of pathogens with AHL-based QS in human health, marine cultures, animals and plants, as well as for the inhibition of the formation of biofilms formed by QS controlled processes.

Thus, in a preferred embodiment of this aspect of the invention, the bacterial cell of the genus *Tenacibaculum* with deposit number CECT 7426, the crude cellular extract or its cultivation supernatants, or any of their combinations, is used for quorum quenching. In a more preferred embodiment, it is used for degrading N-acyl homoserine lactones. In another even much more preferred embodiment, it is used for the manufacture of a medicament. In another even more preferred embodiment, the medicament is used for the treatment of infectious bacterial diseases. In another preferred embodiment, it is used to inhibit the formation of biofilms. In another even more preferred embodiment, it is used in combination with antibiotics or other antibacterial agents. In an even more preferred embodiment, the bacteria causing the infectious disease or formation of the biofilm are Gram negative bacteria.

Another aspect of the invention relates to a composition, hereinafter composition of the invention, comprising:
 a. a bacterial cell belonging to the genus *Tenacibaculum*,
 b. the crude cellular extract of a bacterial culture of the bacterial cell of a),
 c. the supernatant of the bacterial culture of a),
or any of their combinations, for its use as an antibacterial agent.

An antibacterial agent is a natural chemical substance (synthesized by fungi or bacteria) that inhibits growth (bacteriostatic) or kills the bacteria (bactericide).

Another aspect of the invention relates to the use of the composition of the invention, comprising:
 a. a bacterial cell belonging to the genus *Tenacibaculum*,
 b. the crude cellular extract of a bacterial culture of the bacterial cell of a),
 c. the supernatant of the bacterial culture of a),
or any of their combinations, for the manufacture of a medicament.

In a preferred embodiment, the composition of the invention is used for the treatment of bacterial infections. In another preferred embodiment, the composition of the invention is used for the manufacture of a medicament for the treatment of bacterial infections. Bacterial biofilms are a common cause of bacterial infections, both in humans (Costerton et al., 1999. *Science* 284: 1318-1322), and in animals and plants. In another preferred embodiment, the composition of the invention is used to inhibit the formation of biofilms. In another preferred embodiment, the composition of the invention is used in combination with other antibacterial agents. In an even more preferred embodiment, the bacteria that cause the formation of biofilm and/or infection are Gram negative bacteria.

The term "medicament", as used in this specification, makes reference to any substance used to prevent, diagnose, relieve, treat or cure diseases in humans, animals and plants. In the context of the present invention, the diseases are caused by infection with pathogenic bacteria.

The term "infection" is the clinical term to describe the colonization of the host organism by organisms of other species. In the clinical use of the term "infection", the colonizing organism is harmful for the normal functioning and survival of the host, so that the microorganism is classified as pathogen.

The term "genus", as used in this specification, makes reference to the category of the biological classification (taxonomic category) comprising one or more species phylogenetically related and morphologically similar. It is also expected that they share similar chemical and metabolic characteristics.

"Taxonomic category" is understood to be the level of hierarchy used to classify the organisms.

The term "polynucleotide", as used in this specification, relates to a polymer form of nucleotides of any length, whether ribonucleotides or deoxyribonucleotides. The terms "polynucleotide" and "nucleic acid" are used interchangeably and exclusively refer to the primary structure of the molecule.

The term "homology", as used in this specification, makes reference to the similarity between two structures due to a common evolutionary ancestry and, more specifically, to the similarity between the nucleotides of two or more polynucleotides.

The term "identity", as used in this specification, makes reference to the proportion of identical nucleotides between two homologous polynucleotides that are compared.

The term "genotype", as used in this specification, makes reference to the hereditary or genetic constitution of an individual; all genetic material contained in a cell which is generally called nuclear material.

The term "phenotype", as used in this specification, relates to the total sum of structural and functional properties that can be observed in an organism; product of the interaction between the genotype and the environment.

The term "type species" makes reference to the species designated as the type of a genus or subgenus, "type", from the taxonomic standpoint, being the simple element of a taxon whereto the name is permanently assigned and whereon the descriptive characteristics that meet the availability or valid publication details are based.

The culture medium used for the growth of the bacterial cells may be any medium known in the state of the art. Preferably the medium contains the components comprising the environment wherefrom the sample is taken. For example, the culture medium of marine bacteria preferably contains marine salts. The solid support to grow isolated colonies may be agar, noble agar, Gelrite or any other solid medium known in the state of the art.

Throughout the description and the claims, the word "comprises" and its variants are not intended to exclude other technical characteristics, additives, components or steps. For persons skilled in the art, other objects, advantages and characteristics of the invention will be inferred in part from the description and in part from the practice of the invention. The following examples and drawings are provided by way of illustration, and are not intended to be limiting of the present invention.

DETAILED EXPLANATION OF EMBODIMENTS

The invention will be illustrated below by assays carried out by the inventors, revealing the specificity and effectiveness of different strains of different species of the genus *Tenacibaculum* for degrading N-acyl homoserine lactones.
Methodology of Isolation of Marine Bacterial Strains In order to detect marine bacteria with quorum quenching (QQ) activity of AHL type signals, colonies from samples of different marine media samples were isolated.

Three types of samples were taken with sterile material:
Sample of sediment from a tank of a marine closed fish culture circuit at the University of Santiago de Compostela.
Sample of wall biofilm from an outdoor concrete tank that was used as a reservoir of filtered seawater for an aquaculture facility at the IGAFA institute (Arosa Island).
Sample from the seaweed *Fucus* sp. obtained from the rocks of the intertidal zone in Arosa Island. One gram of the algae was sliced and diluted in 10 ml of sterilized sea water.

The solid media used for the isolation were: Tryptic soy agar (TSA), 1% NaCl, Marine agar (MA, Difco), Marine agar in 1/100 dilution, FAS medium supplemented with 1 g/L of casamino acids (FAS CAS) (Schut et al., 1993. *Appl Environ Microbiol* 59: 2150-2160) and FAS medium supplemented with 0.5 g/L of the agarose, chitin and starch polymers (FAS POL) (Bruns et al., 2002. *Appl Environ Microbiol* 8: 3978-3987). A total of 3 dilutions were prepared (1/10, 1/100 and 1/1000) in sterilized sea water for each of the samples and seeded on plates with said culture media. The plates were incubated at 15° C. and 22° C. during 15 days. A total of 165 colonies were isolated depending on their different morphology and tonality for the analysis of QQ activity. Since the 165 strains obtained could grow in MA at 22° C., these culture conditions were selected as standard culture method and for their maintenance in the laboratory.
Detection of QQ Activity The 165 strains isolated were assayed for their QQ activity using two types of assays: in liquid and solid medium.

The AHLs that were used in the liquid assay in order to detect the degrading/inhibiting capacity of the strains were N-Butyryl-L-homoserine lactone (C4-HSL) as representative of the short-chain AHLs and N-Dodecanoyl-L-homoserine lactone (C12-HSL) as representative of long-chain AHLs. In order to quantify the AHLs, two biosensors of *E. coli* JM109 were used, each one transformed with a carrier plasmid of the lux operon, for the detection of C4-HSL (pSB536) and for the detection of C12-HSL (pSB1075). The biosensors were cultivated at 37° C. in LB medium supplemented with the suitable antibiotic (Winson et al., 1998. *FEMS Microbiol Lett* 163: 185-192).

Each marine isolate was inoculated in eppendorf tubes with 1 mL of Marine Broth (MB) and incubated at 22° C. and 200 rpm. After 24 hours of incubation, the culture was divided into two microtubes and centrifuged at 2000×g for 5 min. The corresponding pellets were resuspended in fresh MB with 50 μM C4-HSL or C12-HSL and incubated for another 24 hours at 22° C. and 200 rpm to allow the possible degradation of the AHLs. Once incubated, the cultures were centrifuged at 2000×g, 5 min and 10 μL of supernatant were pipetted on a microtiter plate in order to quantify the AHL activity. This was measured by adding 90 μL of a 1/100 dilution of 12-hour cultures at 37° C. 200 rpm of the biosensor strains based on lux, *E. coli* JM109 pSB536 or pSB1075 stated above, using a luminometer (Ultra Evolution Xfluor4beta E 4.51e) after 4 hours of incubation at 37° C. of the microtiter plates. Different plates were used for each AHL and biosensor. Wells were used as controls with 10 μL of MB with and without 50 μM C4-HSL or C12-HSL.

For the solid assay, two biosensors were used derived from the species *Chromobacterium violaceum* wherein the production of the exopigment violacein is dependent on the presence of AHLs in the culture medium. The strain *C. violaceum* CV026 was initially used to check the results obtained in the bioassays performed in liquid medium with the strains of *E. coli*, making it possible to detect the degradation of N-hexanoyl-L-homoserine lactone (C6-HSL, McClean et al., 1997. *Microbiol* 143: 3703-3711). Later, the degradation capacity of C10-HSL was confirmed using the strain *C. violaceum* VIR07 (Morohoshi et al., 2008. FEMS *Microbiol Lett* 279: 124-130). The isolated marine strains were inoculated in tubes with 1 mL of MB at 22° C. and 200 rpm. After 24 hours, 500 μL of the cultures were centrifuged at 2000×g for 5 min, resuspended in 500 μL of MB whereto 2 μM C6-HSL or C10-HSL were added, and incubated for another 24 hours. In order to evaluate the degradation of the AHLs, 50 μL of the supernatants of these cultures were placed in wells that were made with a punch in plates of LB covered with soft LB inoculated with 500 μL of a 12-hour culture of *C. violaceum* CV026 or *C. violaceum* VIR07, and 50 μL of sterile distilled water were added in order to complete the well volume. After 24 hours of incubation at 25° C., the production of violacein was observed.

In some cases, in order to detect the degradation of long-chain AHLs, the violacein production inhibition assay was used with the strain *C. violaceum* CV026 (FIG. 1B). In this case, in order to evaluate the degradation of C10-HSL, plates of LB were prepared and covered with soft LB inoculated with the sensor strain whereto its corresponding AHL, C6-HSL, was added. In this case the presence of C10-HSL produces an inhibition halo in the production of violacein induced by C6-HSL. The degradation of C10-HSL is detected in this assay by the disappearance or decrease of the inhibition halo (McClean et al., 1997. *Microbiol* 143: 3703-3711).

The identification of the bacterial strain which degraded AHLs was performed by direct PCR amplification of the 16S rRNA gene, partial sequencing thereof (with readings in two directions) and sequence analysis.

Next, a BLAST analysis of the sequences was carried out against the NCBI databases, including the extension of the overlapped fragment, the percentage of similarity and the name of the microorganism with the greatest degree of sequence identity. Thus, the 2OJ strain was identified as *Tenacibaculum discolor* with a similarity of 1018/1019 pb (99.9%) over the sequence AM411030 (type strain DSM 18842).

Figure 2:
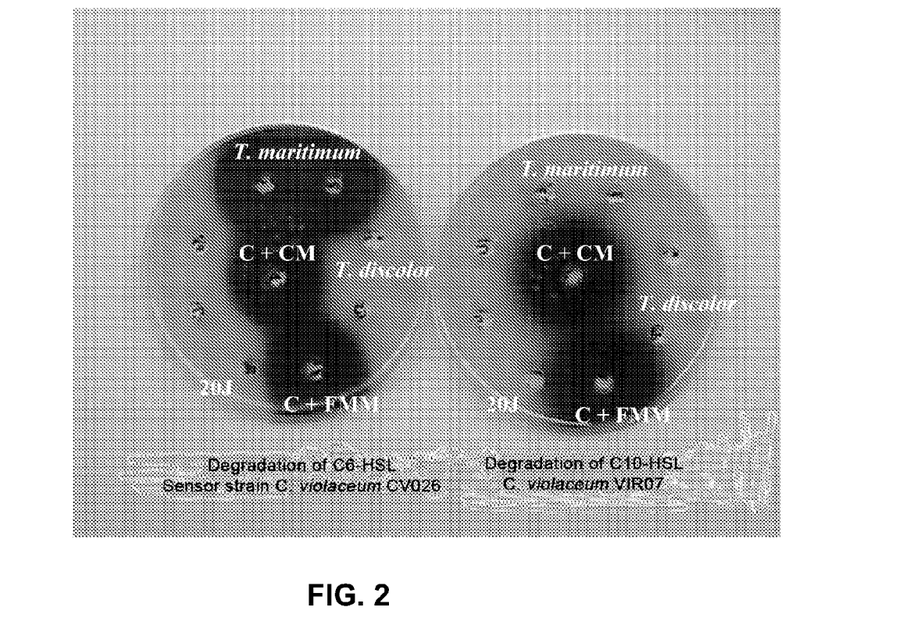
FIG. 2. Assay with the *Chromobacterium violaceum* CV026 and *C. violaceum* VIR07 biosensor strains to detect degradation by *Tenacibaculum discolor* 2OJ and *T. maritimum* of 2 μM C6-HSL (A) and C10-HSL (B), showing that *T. maritimum* does not degrade C6-HSL.
Figure 3:
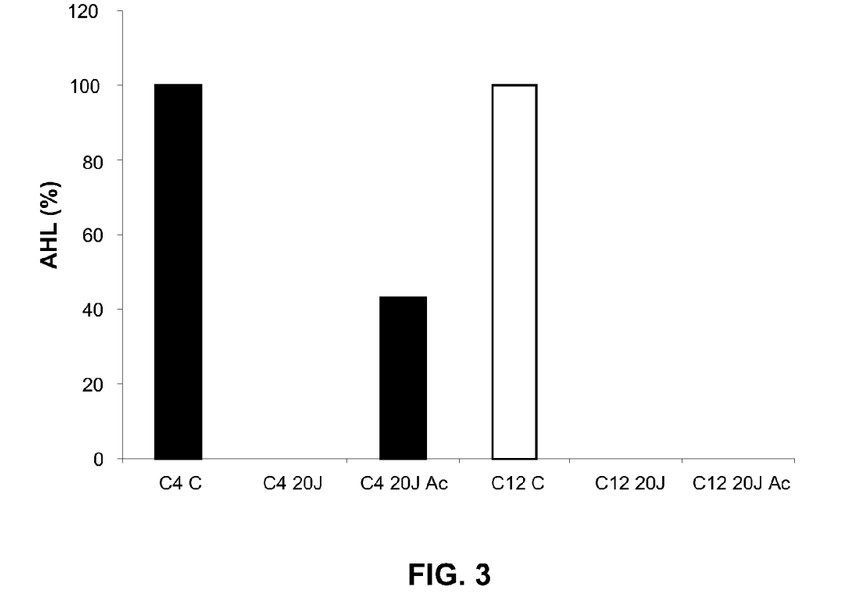
FIG. 3. Percentage of degradation of C4-HSL (black bars) and C12-HSL (white bars) by *Tenacibaculum discolor* 2OJ without and with acidification (Ac) in relation to controls (C) (50 μM) quantified by LC-MS.

Additionally, other strains of different species of the same genus were assayed (Table 2) to see if they showed AHL degradation activity. All the strains and species assayed degraded both C6-HSL and C10-HSL, with the exception of *T. maritimum*, which did not degrade C6-HSL (FIG. 2).

TABLE 2

Strains of different species of the genus *Tenacibaculum* that were assayed.

| STRAIN | C6-HSL | C10-HSL |
|---|---|---|
| *T. maritimum* NCIMB2154 | − | + |
| *T. discolor* 2OJ (own isolate) | + | + |
| *T. discolor* DSM 18842 | + | + |
| *T. soleae* NCIMB 14368 | + | + |
| *T. gallaicum* DSM 18841 | + | + |

Specificity of QQ Activity

*Tenacibaculum discolor* 2OJ was selected as it was the only isolate with QQ activity against the three initially tested AHLs (C4-HSL, C6-HSL and C12-HSL), in order to determine the type of QQ activity that it showed as well as its specificity against a wider range of side-chain length of AHL by LC-MS, an analytical technique that makes it possible to unequivocally verify AHL degradation.

The strain was inoculated in 20 mL of MB and incubated at 22° C. and 200 rpm; after 24 h, 500 μL samples were taken for their centrifugation. The pellets were resuspended in 500 μL of MB, with 50 μM AHL (C4-HSL, C6-HSL, C8-HSL, C10-HSL, C12-HSL or C14-HSL) and incubated another 24 hours at 22° C. and 200 rpm. The supernatants (2000×g 5 min) of these cultures were extracted three times with the same volume of ethyl-acetate and evaporated under a nitrogen flow. The dry extract obtained was resuspended in 200 μL of acetonitrile and the AHLs were quantified by LC-MS. Likewise, control samples were extracted with 500 μL of MB plus 50 μM AHL.

The LC system used was an Agilent 1100 series (Agilent Technologies, Santa Clara, Calif., USA), with a column Zorbax Eclipse XDB-C18, 150×4.6 mm (particle size 5 μm). The mobile phase was 0.1% formic acid in water (A) and methanol (B), and the flow rate 0.4 mL/min. The gradient established was 50% B from 0 to 10 min, followed by a linear gradient of 50 at 90% B for 15 min, followed by 90% B for 25 min (Morin et al., 2003. *J Chromatogr A*, 1002:79-92). The column was rebalanced for 4 min. Twenty microlitres of sample diluted in 0.1% formic acid in acetonitrile were injected into the column. The MS used was an API4000 triple-quadrupole with linear ion trap (Applied Biosystem, Foster City, Calif., USA), in positive ion electrospray mode. Synthetic AHLs with chain lengths from 4 to 14 carbons were used as standards for identification and quantification of the AHLs present in the samples. The quantification of AHLs in the samples was performed by extrapolation from calibration curves obtained from the abundance of the molecular ions obtained for each standard AHL with known concentration (Milton et al., 2001. *J Bacteriol* 183: 3537-3547).

In order to determine the type of degrading enzymatic activity of AHLs (acylase or lactonase) present in *Tenacibaculum discolor* 2OJ, two types of assays were carried out: duplicates of the previously described cultures whereto C4-HSL and C12-HSL had been added were acidified to pH 2.0 with 1M HCl and incubated for a further 24 hours in the same conditions for a subsequent extraction of AHLs and quantification by LC-MS. The acidification of the culture medium enables the recovery of AHL activity only in the case that the molecule had been degraded by lactonase (Yates et al., 2002. *Infect Immun* 70: 5635-5646). In parallel, a solid assay was performed with *C. violaceum* CV026 for the AHLs: C6-HSL, C10-HSL and C12-HSL, with and without acidification to pH 2.0 (Yates et al., 2002. *Infect Immun* 70: 5635-5646).

Kinetics of AHL Degradation

A total of 60 mL of MB inoculated with *Tenacibaculum discolor* 2OJ were incubated at 22° C. and 200 rpm. After 24 hours, the culture was divided and centrifuged (2000×g 5 min), and the pellet was washed twice with 10 mL of PBS pH 6.5. In the two cell suspensions thus obtained, C4-HSL or C12-HSL was added to a final concentration of 30 μM. The reaction mixtures were incubated at 22° C. and 200 rpm for 24 hours and 500 μL samples were taken at different times from time 0.

These samples were taken by using the aforementioned process and the concentrations of C4-HSL or C12-HSL remaining in each sample were determined by LC-MS (Milton et al., 2001. *J Bacteriol* 183: 3537-3547).

Location of AHL Degradation Activity

In order to determine the cell location of the AHL degrading activity, the supernatant and crude cellular extract (CCE) were obtained from a 24-hour culture of *Tenacibaculum discolor* 2OJ in 15 mL of MB. The culture was centrifuged for 5 minutes at 2000×g in order to separate the biomass from the culture medium. The supernatant was filtered through a 0.22 μm filter and stored at 4° C. until it was used. The pellet was washed with 15 mL of PBS pH 6.5, resuspended in another 5 mL of the same buffer, sonicated for 5 minutes in ice and centrifuged at 16000×g for 90 min at 4° C. The CCE thus obtained was filtered through a 0.22 μm filter and stored at 4° C. (Uroz et al., 2005. *Microbiol* 151: 3313-3322).

Two assays were performed with the supernatant and the CCE of *Tenacibaculum discolor* 2OJ:

A solid assay with *C. violaceum* CV026 as previously described. A total of 500 μL of supernatant and CCE were incubated for 24 hours with 20 μM C6 or C10-HSL at 22° C. and 200 rpm. The controls were incubated in the same way, with 500 μL of MB or PBS 20 μM C6 or C10-HSL.

Another assay with 500 μL of supernatant and CCE incubated for 24 hours with 50 μM C4 or C12-HSL at 22° C. and 200 rpm with or without acidification to pH 2.0 with 1M HCl (a further 24 hours at 22° C. and 200 rpm). The AHL concentrations after this assay were quantified by LC-MS as previously described. The results were compared with the degradation of the complete culture (living bacteria) incubated under the same conditions and with fresh MB controls with 50 μM C4 or C12-HSL.

The invention claimed is:

1. A medicament comprising a crude cellular extract of the strain *Tenacibaculum* CECT 7426 in an amount effective to degrade C10-HSL quorum sensing signals.

2. A composition comprising a crude cellular extract of the strain *Tenacibaculum* CECT 7426 in an amount effective to degrade C10-HSL quorum sensing signals.

3. A biologically pure culture of the strain *Tenacibaculum* CECT 7426 that degrades C10-HSL quorum sensing signals.

* * * * *